US00PP31287P3

(12) United States Plant Patent
Pitiot et al.

(10) Patent No.: US PP31,287 P3
(45) Date of Patent: Dec. 31, 2019

(54) APPLE TREE NAMED 'INOBI'

(50) Latin Name: ***Malus domestica* Borkh.**
Varietal Denomination: Inobi

(71) Applicant: NOVADI SARL, Lyons (FR)

(72) Inventors: Christelle Pitiot, Lyons (FR); François Laurens, Beaucouze (FR)

(73) Assignees: Novadi SARL, Lyons (FR); Institut National de la Recherche Agronomique (INRA), Paris (FR)

( * ) Notice: Subject to any disclaimer, the term of this patent is extended or adjusted under 35 U.S.C. 154(b) by 0 days.

(21) Appl. No.: 16/350,437

(22) Filed: Nov. 13, 2018

(65) Prior Publication Data

US 2019/0150338 P1 May 16, 2019

(30) Foreign Application Priority Data

Nov. 14, 2017 (FR) ..... 20784

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

*Primary Examiner* — Susan McCormick Ewoldt
(74) *Attorney, Agent, or Firm* — Michelle Bos Legal LLC

(57) ABSTRACT

A new apple tree named 'Inobi' notable for its attractive fruit, favorable organoleptic qualities and resistance to apple scab. Fruit of 'Inobi' is highly colored and has a long shelf life.

8 Drawing Sheets

Latin name: *Malus domestica* Borkh.
Variety denomination: 'Inobi'.

BACKGROUND OF THE VARIETY

'Inobi' is a new and distinct cultivar of apple tree (*Malus domestica* Borkh). This new cultivar is a product of a controlled cross of 'Pilot' (not patented) x 'X6398' (not patented), carried out at Angers, France in 1995. 'Inobi' was initially selected for propagation and further experimentation because of its attractive fruit, favorable organoleptic qualities and resistance to apple scab. The variety was first asexually reproduced by grafting at Saint Laurent des Vignes, France in 1998. 'Inobi' has been observed to remain true to type over successive asexually propagated generations.

BRIEF DESCRIPTION OF THE VARIETY

'Inobi' is notable for its resistance to scab, and for its high quality fruit, which is highly colored and has a long shelf life. The new variety is distinguished from female parent 'Pilot' by its earlier maturity (20 days before 'Pilot'), more colorful fruit, and scab resistance. 'Inobi' is distinguished from 'X6398' by its more colorful fruit, improved shelf life, and later maturity (14 days after 'X6398').

BRIEF DESCRIPTION OF THE PHOTOGRAPHS

Figure 1:
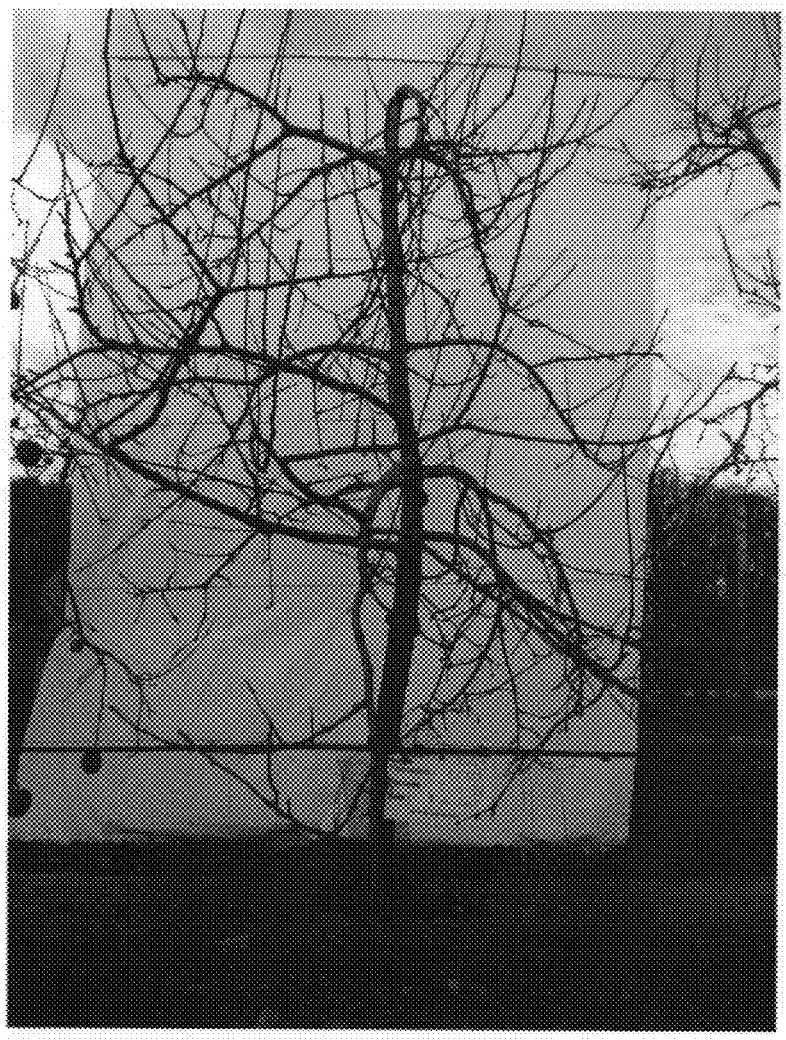
Figure 2:
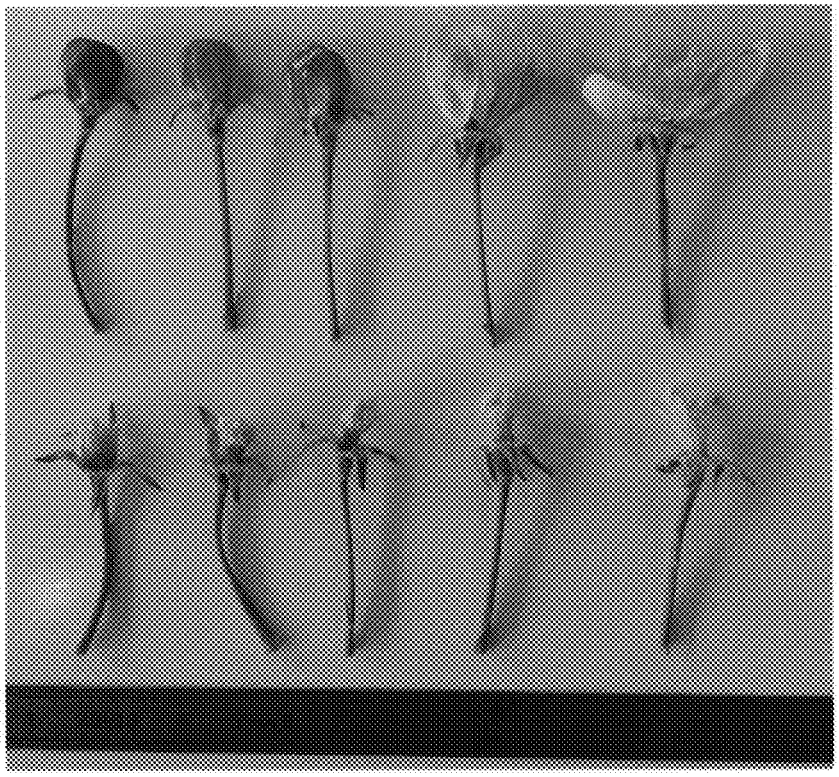
Figure 3:
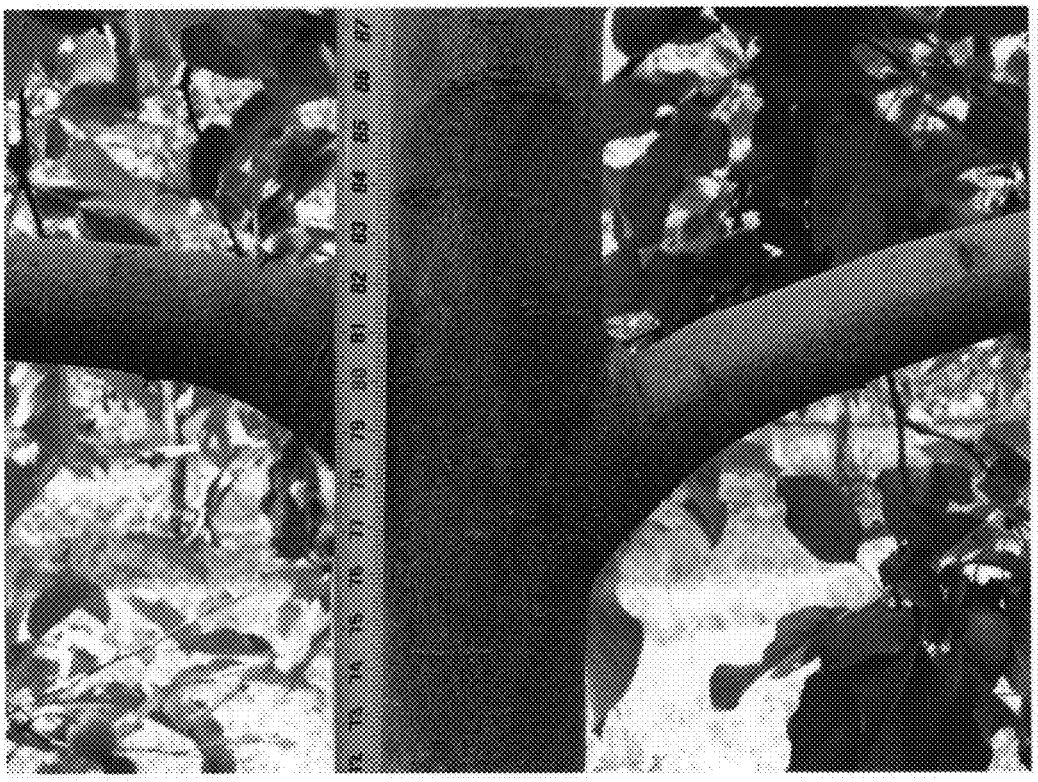
Figure 4:
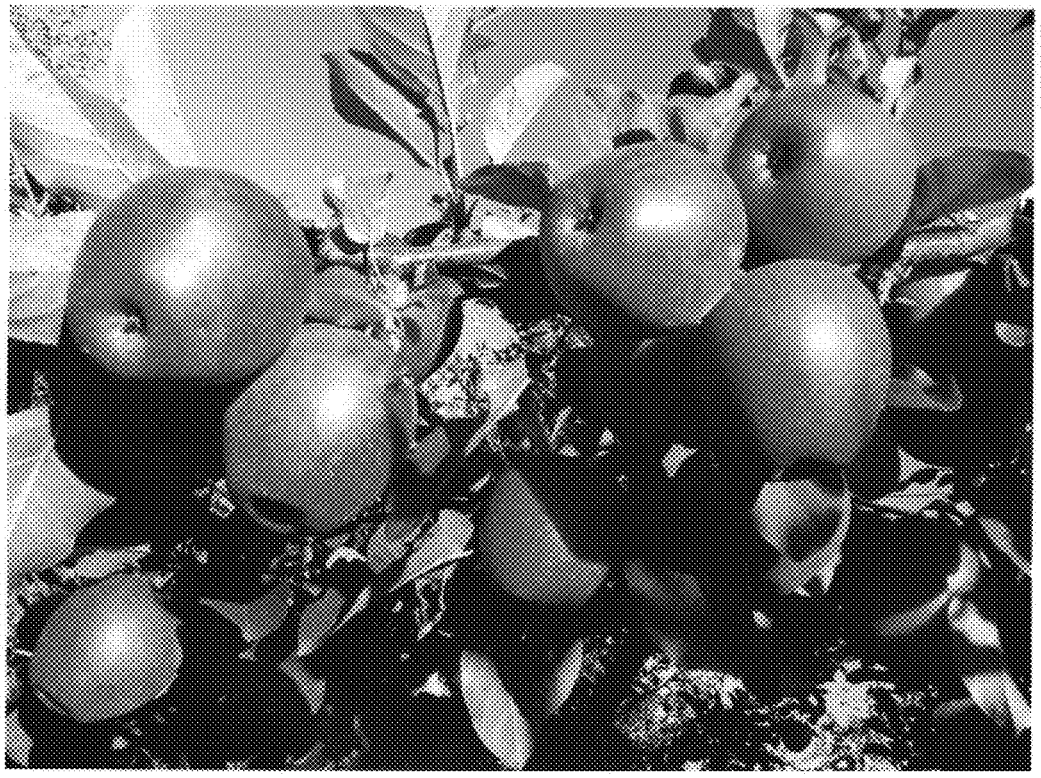
Figure 5:
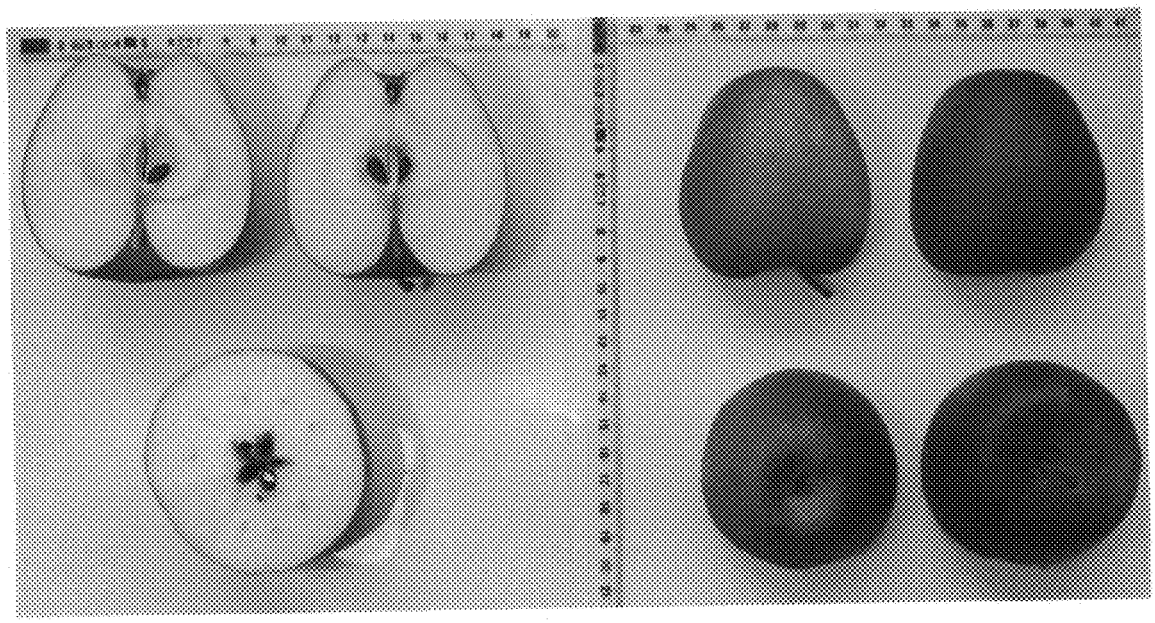
Figure 6:
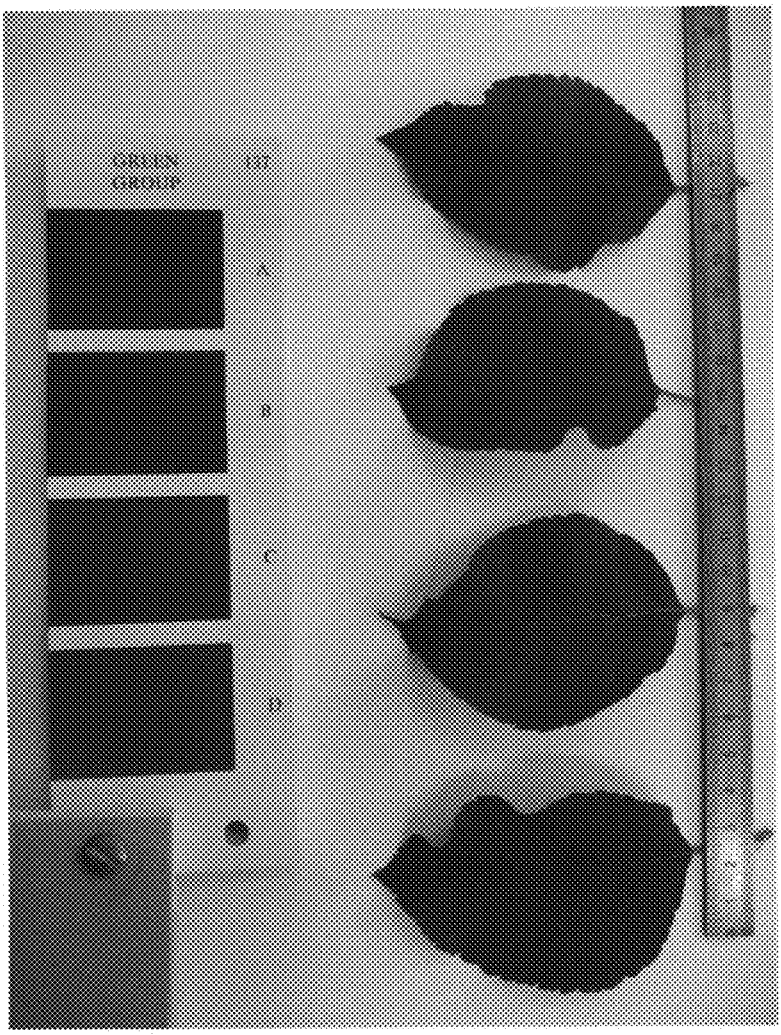
Figure 7:
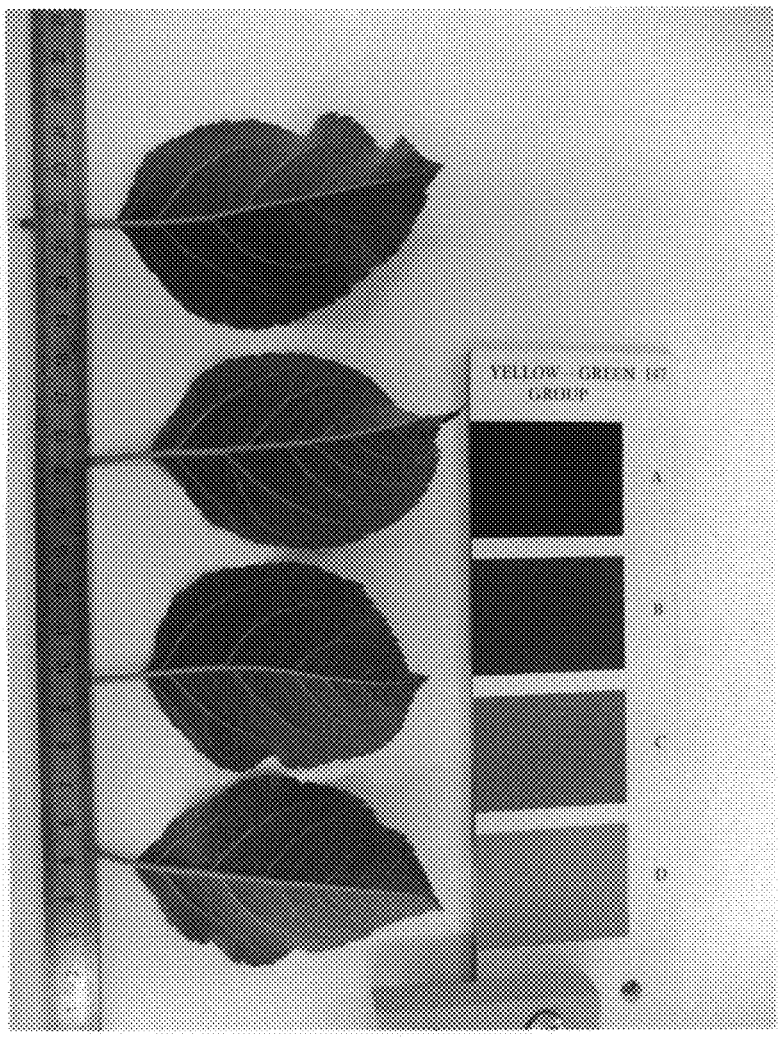
Figure 8:
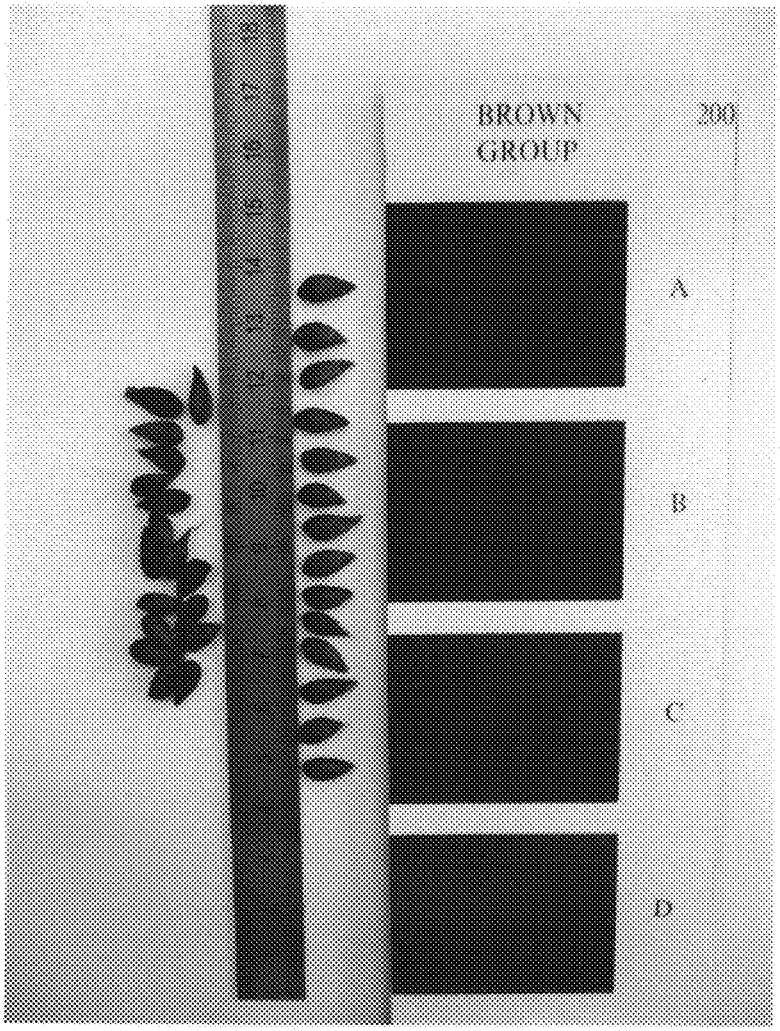

FIG. 1 shows the tree and branches of the new variety;
FIG. 2 shows the buds and blossoms of the new variety;
FIG. 3 shows the trunk and branches of the new variety;
FIG. 4 shows fruit of the new variety on the tree;
FIG. 5 shows whole and sectioned fruit of the new variety;

FIG. 6 shows the upper surface of the leaves of the new variety;
FIG. 7 shows the lower surface of the leaves of the new variety; and
FIG. 8 shows the seeds of the new variety.

DETAILED BOTANICAL DESCRIPTION OF THE VARIETY

The following-detailed botanical description is based on observations of seven-year-old trees of 'Inobi' planted in 2011. The trees were grown at Champagne, France on Pajam®2 Cepiland rootstock. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor*.—Average.
*Type*.—Ramified.
*Habit*.—Spreading to drooping.
*Height*.—4 m.
*Diameter*.—1.5 m.
*Trunk diameter* (30 *cm above graft union*).—67 mm.
*Bark texture*.—Slightly rough.
*Bark coloration*.—Greyed-green 197B.
*Lenticels*.—Greyed-orange 164B ; height 0.9 mm to 1.7 mm; length 1.4 mm to 5.8 mm.

Branch (fruiting branches located at around 1 m above the graft union):
- *Length.*—1.1 m to 1.5 m.
- *Diameter.*—29 mm to 32 mm.
- *Crotch angle.*—80° to 90°.
- *Coloration.*—Greyed-green 197B.
- *Lenticels.*—Greyed-orange 164B; height 0.8 mm to 1.2 mm; length 1 to 4.3 mm; 0 to 3 per $cm^2$.

1 Year old shoot:
- *Length.*—48 cm to 55 cm.
- *Coloration.*—Greyed-purple 183A.
- *Pubescence.*—Weak.
- *Thickness.*—3.9 mm.
- *Internode length.*—37 mm.
- *Lenticels.*—Greyed-yellow 162C; height 0.8 mm; length 1.8 mm to 2.4 mm; 4 to 6 per $cm^2$.

Winter hardiness:
- *Hardiness* (*climate suitability*).—Temperate.

Flowers:
- *Color* (*balloon stage*).—Greyed-purple 186B.
- *Diameter of open flower.*—43 mm to 47 mm.
- *Relative position of petal margin.*—Not touching.
- *Flower depth.*—16.6 mm from the bottom of the ovary to the top of the style.
- *Number per cluster.*—5 to 6.
- *Bloom date* (2017 *growing season*).—First bloom April 5 (3 days after 'Golden Delicious'); full bloom April 8 (2 days after 'Golden Delicious').

Petals:
- *Number per flower.*—5.
- *Shape.*—Oval.
- *Length.*—21.5 mm+/−0.3 mm.
- *Width.*—16 mm+/−0.5 mm.
- *Apex.*—Rounded.
- *Base.*—Cuneate.
- *Margin.*—Smooth.
- *Color.*—Upper surface — Greyed-purple 186D.
- *Color.*—Lower surface — Greyed-purple 186C.
- *Pistils.*—Length 14.4+/−2 mm; yellow-green 145B.
- *Anthers.*—About 20; length 2.4 mm; pollen yellow 10B.
- *Stigma.*—1.0+/−0.2 mm; yellow green 144C.
- *Style.*—Length 8.3+/−0.2 mm; yellow-green 145B.
- *Ovary.*—Length 4 mm.
- *Pedicel.*—Length 44 mm+/−2 mm; diameter 1.6+/−0.2 mm; green 143C.
- *Sepals.*—Quantity 5; length 8.9 mm; pointed; green 143A.

Leaves:
- *Length* (*petiole not included*).—9.6 cm.
- *Width.*—5.6 cm.
- *Length/width ratio.*—1.7.
- *Shape.*—Oval.
- *Blade margin.*—Serrate.
- *Apex shape.*—Acuminate.
- *Base shape.*—Rounded.
- *Color.*—Upper surface — Green 137A.
- *Color.*—Lower surface — Yellow-green 147B.
- *Attitude in relation to shoot.*—Upward, 55°.

Petiole:
- *Length.*—25 mm.
- *Diameter.*—1.9 mm.
- *Coloration.*—Yellow-green 144A and 144C.

Fruit:
- *Quantity per cluster.*—1 to 2.
- *Size.*—70 to 80 mm (76% of harvest).
- *Weight.*—195 g.
- *General shape in profile.*—Conic.
- *Position of maximum diameter.*—In the middle of the fruit.
- *Ribbing.*—Very weak.
- *Crowning at calyx end.*—Weak.
- *Aperture of eye.*—Average.
- *Length of sepal.*—5 mm to 8.8 mm.
- *Depth of eye basin.*—12 mm.
- *Width of eye basin.*—28 mm.
- *Length of stalk.*—39 mm.
- *Thickness of stalk.*—1.8 mm to 2.2 mm.
- *Width of stalk cavity.*—35 mm.
- *Depth of stalk cavity.*—16 mm.
- *Size of lenticels.*—0.5 mm.
- *Bloom of skin.*—None.
- *Greasiness of skin.*—Low.
- *Background color of skin.*—Yellow-orange 15D.
- *Overcolor of skin.*—Red 45A.
- *Amount of overcolor.*—Large, 75% to 100%.
- *Intensity of overcolor.*—High.
- *Pattern of overcolor.*—Solid flush with weakly defined stripes.
- *Flesh texture.*—Average fineness.
- *Aroma.*—Balanced.
- *Juiciness.*—Average.
- *Brix.*—13.5°.
- *Flesh color.*—Yellow-white 158A.
- *Stem color.*—Greyed-red 178B.

Seeds:
- *Quantity per fruit.*—7.
- *Shape.*—Long, narrow and pointed.
- *Color.*—Brown 200C.

Harvest:
- *Fruit production per tree per harvest.*—32 kg.
- *Harvest date* (2017 *growing season*).—September 8 (6 to 10 days before 'Golden Delicious').

Diseases/pests:
- *Resistance.*—Resistance to scab (strains EUB04 and EU1127).
- *Susceptibility.*—None noted.

Market use: Fresh market.

The invention claimed is:

1. A new and distinct apple tree substantially as described and illustrated herein.

* * * * *